(12) United States Patent
Lee et al.

(10) Patent No.: US 7,470,770 B2
(45) Date of Patent: Dec. 30, 2008

(54) GENE ENCODING MALIC ENZYME AND METHOD FOR PREPARING SUCCINIC ACID USING THE SAME

(75) Inventors: Sang Yup Lee, Daejeon (KR); Hyohak Song, Daejeon (KR); Yu Sin Jang, Daejeon (KR); Jeong Wook Lee, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 272 days.

(21) Appl. No.: 11/229,368

(22) Filed: Sep. 16, 2005

(65) Prior Publication Data

US 2007/0042476 A1 Feb. 22, 2007

(30) Foreign Application Priority Data

Aug. 19, 2005 (KR) ...................... 10-2005-0076301

(51) Int. Cl.
*C07K 14/00* (2006.01)
*C12N 15/11* (2006.01)
*C12N 15/63* (2006.01)
*C12N 1/20* (2006.01)
*C12P 13/20* (2006.01)

(52) U.S. Cl. ................... 530/350; 536/23.1; 435/320.1; 435/252.1

(58) Field of Classification Search ........................ None
See application file for complete search history.

(56) References Cited

U.S. PATENT DOCUMENTS 5,143,834 A 9/1992 Glassner et al.
5,168,055 A 12/1992 Datta et al.
5,504,004 A 4/1996 Guettler et al.
5,521,075 A 5/1996 Guettler et al.
5,770,435 A 6/1998 Donnelly et al.

FOREIGN PATENT DOCUMENTS

WO WO 2005/052135 A1 6/2005

OTHER PUBLICATIONS

STIC Search Report "us-11-229-368.4.rup". pp. 1-4.*
STIC Search Report "us-11-229-368-3.rge". pp. 1-5.*
Kobayashi et al. J. Biol.Chem. Structure and Properties of malic enzyme from *Bacillus stearothernophilus*. 264(6): 3200-3205, 1989.*
Zeikus et al., *Appl. Microbiol. Biotechnol.*, 51:545, 1999.
Willke et al., *Appl. Microbiol. Biotechnol.*, 66:131, 2004.
Hong et al., *Biotechnol. Lett.*, 22:871, 2000.
Laivenieks et al., *Appl. Environ. Microbiol.*, 63:2273, 1997.
Hong et al., *Nature Biotechnol.*, 22:1275, 2004.
Kehrenberg et al., *J. Antimicrob. Chemother.*, 49:383, 2002.
Phue et al., *Biotechnol. Bioeng.*, 90:805, 2005.
Van der Werf et al., *Arch. Microbiol.*, 167:332, 1997.

* cited by examiner

*Primary Examiner*—David Guzo
*Assistant Examiner*—Michele K. Joike
(74) *Attorney, Agent, or Firm*—Kelly Reynolds; Steven J. Hultquist; Intellectual Property/Technology Law

(57) ABSTRACT

A nucleotide sequence encoding a malic enzyme and a method for preparing succinic acid using the same, more particularly, a maeB nucleotide sequence encoding a malic enzyme B having the activity of converting pyruvic acid or pyruvate to malic acid or malate, or vice versa, a recombinant vector containing the gene, a microorganism transformed with the recombinant vector, and a method for preparing succinic acid using the transformed microorganism.

14 Claims, 3 Drawing Sheets

SEQUENCE LISTING

```
<160> NUMBER OF SEQ ID NOS: 4

<210> SEQ ID NO 1
<211> LENGTH: 28
<212> TYPE: DNA
<213> ORGANISM: Artificial Sequence
<220> FEATURE:
<223> OTHER INFORMATION: Synthetic Construct

<400> SEQUENCE: 1
cgggatccgg tgaatttcca ttgttaac                                          28

<210> SEQ ID NO 2
<211> LENGTH: 29
<212> TYPE: DNA
<213> ORGANISM: Artificial Sequence
<220> FEATURE:
<223> OTHER INFORMATION: Synthetic Construct

<400> SEQUENCE: 2
cgggatccac aaaagaaaag tctgctatc                                         29

<210> SEQ ID NO 3
<211> LENGTH: 2271
<212> TYPE: DNA
<213> ORGANISM: Mannheimia succiniciproducens MBEL55E

<400> SEQUENCE: 3
atggacgaac aattacgtca agccgcatta gattttcatg aatttccggt tcccggaaag        60
atcgaagtta ccccgactaa atcacttgcc actcaacgtg accttgcact ggcttattcg       120
ccgggcgttg caatgccctg tttagaaatt caagaagatc cggcaaaagc ttataattac       180
accgcaaaag gcaatttagt tgccgtaatt tcaaacggta ccgccgtgtt gggattaggt       240
aatatcggcg ccctcgcagg caaaccggta atggaaggta aaggcgtttt attcaaaaaa       300
ttcgccggcg tagatgtttt tgatattgaa ataaatgaaa aagatccgga aaattagtg        360 gaaattatcg ccgccctcga gccgacattc ggcggtatta atcttgaaga tatcaaagcg       420
cccgaatgtt tttacattga acaaaaatta cgcgagcgca tgaatattcc ggtattccac       480
gatgatcaac acggtacggc gattatcagc tccgctgcgg ttttaaacgg tttacgcatt       540
```

```
attaataaaa aaatcgaaga tgtgcgttta gtggcatccg gtgcgggtgc ggcctctatt      600
gcctgtttaa atctgttggt gtcgttaggg atgaaacgtg aaacattacg gtttgcgac       660
tctaaaggcg ttatttataa aggtcgcgac gaaaatatgg atgcaacaaa aaaactgtat      720
gccattgacg acaacggtac ccgttcatta gccgatgcaa ttccgaatgc ggatattttc      780
ttaggttgct ccgccgccgg cgctttgact caggaaatgg taaaaacaat ggggcctaat      840
ccgttgattc ttgcgttggc taacccgaat ccggaaatta ccgccggaa gcaaaagcg        900
gttcgtcccg acgccatcgt ctgtaccggt cgttcagact ccctaaccaa gtaaataac      960
gtgctgtgct tcccgtttat tttccgcggt gcgctagatg tgggtgcgac acaatcaac     1020
gaagaaatga aaatggcggc ggtgcgcgct attgccgatc ttgcgcttgc gaacaaagc     1080
gatgtggttt cttcagccta cacgacgaa agcgaagtca ctttcgggcc ggaatacgtt     1140
attcctaaac cttttgatcc tcgcttaatt atccgtattg caccggcggt agccaaagcg    1200
gcaatggaca gcggcgtggc aacccgcccg attcaaaatt tcgacgctta tatcgaaaaa    1260
ctcacccaat tcgtttacaa aaccaatctg ttcatgaaac ctgtctttaa tcaggcgaaa    1320
gcggataaaa aacgcgtatt gctcacagac ggcgaagaaa cccgcatttt gcatgcggtg   1380
caagaaattt cgaccttagg aatcgcttat cccgtcttgg tcggacgttt ggatgtgatc    1440
gaagcgcaaa ttaaacgcct cggtttaaaa atccaggcgg gtgtcgattt tgaagtgcta    1500
aatacggata atgaagaaat ctaccaacaa tgctggtcgc tctatcacaa taaactaaaa    1560
cgtcacggcg ttaccgaagc catggcaaaa cgccgtatgt taaccaactc gacggctatc   1620
ggttccgctt tactggaact cggttatgcg gacgcaatgc tttgcggatt agtcggtacc   1680
tattcttcca gcctttcttt attgaaagaa gttatcggca ttaaagaaaa tgtagacatc    1740
ccggcaacgg taaacggatt ggtactgcca agcggcaact tatttatcgc ggatactttc    1800
gttaatttag cgccgacggc ggaagaatta gcggaaatta ccttaatggc ggcggaagaa   1860
gtgcgccgtt tcggtattga accgcaagtg gcgttaattt ctcattctaa tttcggtact    1920
tcggaagatc aaagtgcggt caaaatgcgc gaagttttac aattagtgaa acgcaggcg    1980
cctgatttga tcattgacgg cgaaatgcac gctaatgtag cgttaaatga aatttacgc   2040
cgcgaagtta tgcctgacag tccgctcaaa ggcgcggcaa atctgctcat tatgccggat   2100
atggaatccg cccgtatcag tttgaattta ttacagggca ccgcgacacc gattactatc   2160
ggaccaatcc tgatgggtat gaaaaaaccg gcgcatattt taacttccgt gtcttccgta   2220
cgccgtatta tcaatatggt tgctattgcg gcggttaaag cgcaacaaaa c            2271
```

<210> SEQ ID NO 4
<211> LENGTH: 757
<212> TYPE: PRT
<213> ORGANISM: Mannheimia succiniciproducens MBEL55E

<400> SEQUENCE: 4

```
Met Asp Glu Gln Leu Arg Gln Ala Ala Leu Asp Phe His Glu Phe Pro
1               5                   10                  15

Val Pro Gly Lys Ile Glu Val Thr Pro Thr Lys Ser Leu Ala Thr Gln
            20                  25                  30

Arg Asp Leu Ala Leu Ala Tyr Ser Pro Gly Val Ala Met Pro Cys Leu
        35                  40                  45

Glu Ile Gln Glu Asp Pro Ala Lys Ala Tyr Asn Tyr Thr Ala Lys Gly
    50                  55                  60

Asn Leu Val Ala Val Ile Ser Asn Gly Thr Ala Val Leu Gly Leu Gly
```

-continued

```
            65                  70                  75                  80
Asn Ile Gly Ala Leu Ala Gly Lys Pro Val Met Glu Gly Lys Gly Val
                85                  90                  95
Leu Phe Lys Lys Phe Ala Gly Val Asp Val Phe Asp Ile Glu Ile Asn
            100                 105                 110
Glu Lys Asp Pro Glu Lys Leu Val Glu Ile Ala Ala Leu Glu Pro
            115                 120                 125
Thr Phe Gly Gly Ile Asn Leu Glu Asp Ile Lys Ala Pro Glu Cys Phe
            130                 135                 140
Tyr Ile Glu Gln Lys Leu Arg Glu Arg Met Asn Ile Pro Val Phe His
145                 150                 155                 160
Asp Asp Gln His Gly Thr Ala Ile Ile Ser Ser Ala Ala Val Leu Asn
                165                 170                 175
Gly Leu Arg Ile Ile Asn Lys Lys Ile Glu Asp Val Arg Leu Val Ala
                180                 185                 190
Ser Gly Ala Gly Ala Ala Ser Ile Ala Cys Leu Asn Leu Leu Val Ser
                195                 200                 205
Leu Gly Met Lys Arg Glu Asn Ile Thr Val Cys Asp Ser Lys Gly Val
            210                 215                 220
Ile Tyr Lys Gly Arg Asp Glu Asn Met Asp Ala Thr Lys Lys Leu Tyr
225                 230                 235                 240
Ala Ile Asp Asp Asn Gly Thr Arg Ser Leu Ala Asp Ala Ile Pro Asn
                245                 250                 255
Ala Asp Ile Phe Leu Gly Cys Ser Ala Ala Gly Ala Leu Thr Gln Glu
            260                 265                 270
Met Val Lys Thr Met Gly Pro Asn Pro Leu Ile Leu Ala Leu Ala Asn
            275                 280                 285
Pro Asn Pro Glu Ile Thr Pro Pro Glu Ala Lys Ala Val Arg Pro Asp
            290                 295                 300
Ala Ile Val Cys Thr Gly Arg Ser Asp Phe Pro Asn Gln Val Asn Asn
305                 310                 315                 320
Val Leu Cys Phe Pro Phe Ile Phe Arg Gly Ala Leu Asp Val Gly Ala
                325                 330                 335
Thr Thr Ile Asn Glu Glu Met Lys Met Ala Ala Val Arg Ala Ile Ala
            340                 345                 350
Asp Leu Ala Leu Ala Glu Gln Ser Asp Val Val Ser Ser Ala Tyr Thr
            355                 360                 365
Asp Glu Ser Glu Val Thr Phe Gly Pro Glu Tyr Val Ile Pro Lys Pro
            370                 375                 380
Phe Asp Pro Arg Leu Ile Ile Arg Ile Ala Pro Ala Val Ala Lys Ala
385                 390                 395                 400
Ala Met Asp Ser Gly Val Ala Thr Arg Pro Ile Gln Asn Phe Asp Ala
                405                 410                 415
Tyr Ile Glu Lys Leu Thr Gln Phe Val Tyr Lys Thr Asn Leu Phe Met
            420                 425                 430
Lys Pro Val Phe Asn Gln Ala Lys Ala Asp Lys Arg Val Leu Leu
            435                 440                 445
Thr Asp Gly Glu Glu Thr Arg Ile Leu His Ala Val Gln Glu Ile Ser
            450                 455                 460
Thr Leu Gly Ile Ala Tyr Pro Val Leu Val Gly Arg Leu Asp Val Ile
465                 470                 475                 480
Glu Ala Gln Ile Lys Arg Leu Gly Leu Lys Ile Gln Ala Gly Val Asp
                485                 490                 495
```

-continued

```
Phe Glu Val Leu Asn Thr Asp Asn Glu Glu Ile Tyr Gln Gln Cys Trp
            500                 505                 510

Ser Leu Tyr His Asn Lys Leu Lys Arg His Gly Val Thr Glu Ala Met
            515                 520                 525

Ala Lys Arg Arg Met Leu Thr Asn Ser Thr Ala Ile Gly Ser Ala Leu
            530                 535                 540

Leu Glu Leu Gly Tyr Ala Asp Ala Met Leu Cys Gly Leu Val Gly Thr
545                 550                 555                 560

Tyr Ser Ser Ser Leu Ser Leu Leu Lys Glu Val Ile Gly Ile Lys Glu
                565                 570                 575

Asn Val Asp Ile Pro Ala Thr Val Asn Gly Leu Val Leu Pro Ser Gly
            580                 585                 590

Asn Leu Phe Ile Ala Asp Thr Phe Val Asn Leu Ala Pro Thr Ala Glu
            595                 600                 605

Glu Leu Ala Glu Ile Thr Leu Met Ala Ala Glu Glu Val Arg Arg Phe
            610                 615                 620

Gly Ile Glu Pro Gln Val Ala Leu Ile Ser His Ser Asn Phe Gly Thr
625                 630                 635                 640

Ser Glu Asp Gln Ser Ala Val Lys Met Arg Glu Val Leu Gln Leu Val
                645                 650                 655

Lys Thr Gln Ala Pro Asp Leu Ile Ile Asp Gly Glu Met His Ala Asn
            660                 665                 670

Val Ala Leu Asn Glu Asn Leu Arg Arg Glu Val Met Pro Asp Ser Pro
            675                 680                 685

Leu Lys Gly Ala Ala Asn Leu Leu Ile Met Pro Asp Met Glu Ser Ala
            690                 695                 700

Arg Ile Ser Leu Asn Leu Leu Gln Gly Thr Ala Thr Pro Ile Thr Ile
705                 710                 715                 720

Gly Pro Ile Leu Met Gly Met Lys Lys Pro Ala His Ile Leu Thr Ser
                725                 730                 735

Val Ser Ser Val Arg Arg Ile Ile Asn Met Val Ala Ile Ala Ala Val
                740                 745                 750

Lys Ala Gln Gln Asn
            755
```

GENE ENCODING MALIC ENZYME AND METHOD FOR PREPARING SUCCINIC ACID USING THE SAME

CROSS-REFERENCE TO RELATED APPLICATION

Priority is hereby claimed under 35 USC 119 of Korean Patent Application No. 10-2005-0076301 filed on Aug. 19, 2005 in the Korean Intellectual Property Office. The disclosure of said Korean Patent Application is hereby incorporated herein by reference in its entirety.

BACKGROUND OF THE INVENTION

1. Field of the Invention

The present invention relates to a novel gene encoding a malic enzyme and a method for preparing succinic acid using the same, more particularly, to a maeB gene encoding a malic enzyme B having the activity of converting pyruvic acid or pyruvate to malic acid or malate, or vice versa, a recombinant vector containing the gene, a microorganism transformed with the recombinant vector, and a method for preparing succinic acid using the transformed microorganism.

2. Background of the Related Art

Succinic acid, which is a dicarboxylic acid ($HOOCCH_2CH_2COOH$) with four carbon atoms initially purified from amber resin, is used in a very wide range of industrial applications (Zeikus et al., *Appl. Microbiol. Biotechnol.*, 51:545, 1999). Particularly, as the utility of succinic acid as a main raw material of biodegradable polymers was recently proven, a rapid increase in the demand of succinic acid is expected (Willke et al., *Appl. Microbiol. Biotechnol.*, 66:131, 2004).

Succinic acid can be produced by chemical synthesis and fermentation. Most commercially available succinic acid recently has been produced from n-butane as a starting material derived from LNG or crude petroleum, by chemical manufacturers, such as BASF, DuPont and BP Chemicals. Chemical processes for the synthesis of succinic acid have the problem that they cause the discharge of large amounts of harmful solid wastes, waste solutions and waste gases (including carbon monoxide) during the preparation of succinic acid, and particularly, have the limitation that they use fossil raw material as a basic material. Only a small amount of succinic acid, which is used in special applications, such as medical drugs, is currently produced by traditional microbial processes.

In an attempt to solve the described problems occurring in the chemical processes for the synthesis of succinic acid, studies on the production of succinic acid by fermentation processes have been conducted by many researchers. The method for the production of succinic acid by fermentation is a method of producing succinic acid from renewable raw materials using microorganisms. Bacterial strains which are used in the production of succinic acid can be broadly divided into recombinant *E. coli* and ruminal bacteria, such as *Actinobacillus*, *Anaerobiospirillum*, *Bacteroides*, *Mannheimia*, *Succinimonas*, *Succinivibrio*, etc.

A research team of the University of Chicago has attempted to increase the production of succinic acid by preparing a mutant strain AFP111 (ATCC No. 202021) in which *E. coli* ldh and pfl genes involved in the production of lactic acid and formic acid have been removed and a ptsG gene of the glucose transfer system has been manipulated (U.S. Pat. No. 5,770,435).

Among ruminal bacteria, *Actinobacillus*, *Anaerobiospirillum* and *Mannheimia* strains have been relatively much-studied. Michigan Biotechnology Institute (MBI) has developed an *Actinobacillus succinogenes* 130Z strain (ATCC No. 55618) and a process for producing a high concentration of succinic acid using the same (U.S. Pat. No. 5,504,004). Also, such institute has developed *Anaerobiospirillum succiniciproducens* and its mutant strains, and a process for the production and purification of succinic acid (U.S. Pat. Nos. 5,521,075; 5,168,055; and 5,143,834).

However, the processes for preparing succinic acid using the described strains have low productivity and result in the production of large amounts of byproducts in addition to succinic acid, thus requiring high costs for the separation and purification of succinic acid. Accordingly, there has been an urgent need for the development of a bacterial system that has high productivity and at the same time, can inhibit the production of byproducts (Hong et al., *Biotechnol. Lett.*, 22:871, 2000).

For this purpose, the isolation of an excellent succinic acid-producing bacterial strain, the establishment of genome sequences and the understanding of metabolic characteristics of bacterial strains based on them are first required. With such basis, it then is necessary to secure gene manipulation technologies required for the construction of a novel gene recombinant bacterial strain. Although there has been a prior attempt to increase the production of succinic acid using the phosphoenolpyruvate carboxykinase (pckA) gene of *Anaerobiospirillum succiniciproducens* (Laivenieks et al., *Appl. Environ. Microbiol.*, 63:2273, 1997), the art has failed to develop a gene recombinant strain based on the full genome sequence of ruminal bacteria.

Meanwhile, the present inventors previously isolated a *Mannheimia succiniciproducens* MBEL55E strain from the rumen of a Korean cow that produces succinic acid in high efficiency using various substrates, and reported the full genome sequence of the strain (Hong et al., *Nature Biotechnol.*, 22:1275, 2004). Particularly, the above strain is characterized by immobilizing carbon dioxide, known as a greenhouse gas, in the synthesis of succinic acid. Also, this applicant previously prepared succinic acid with high yield by deleting a lactic acid dehydrogenase gene (ldhA) and a pyruvate formate-lyase (pfl) from *Mannheimia succiniciproducens* MBEL55E, so as to construct mutant strain *Mannheimia* sp. LPK (KCTC 10558BP), and deleting a phosphotransacetylase gene (pta) and an acetate kinase gene (ackA) from the LPK strain to construct mutant strains *Mannheimia* sp. LPK7, and then culturing the resulting mutant strain in an anaerobic condition (WO 05/052135 A1). However, the mutant strain has a problem that it results in the accumulation of malate to a certain degree as a byproduct during the culture thereof.

Accordingly, there continues to be an urgent need in the art for the development of a bacterial system for high productivity, low byproduct succinic acid production that overcomes the deficiencies of the prior art

SUMMARY OF THE INVENTION

The present invention relates to a novel gene encoding a malic enzyme B derived from *Mannheimia succiniciproducens* MBEL55E that is usefully employed in the production of succinic acid.

The present invention relates on one aspect to a recombinant vector containing said gene, and a recombinant microorganism transformed with said recombinant vector.

Still another aspect of the present invention relates to a method for preparing succinic acid using said recombinant microorganism.

In one aspect, the present invention relates to a malic enzyme B having an amino acid sequence of SEQ ID NO: 4, which has the activity of either converting pyruvate to malate or converting malate to pyruvate, as well as a gene (maeB) encoding the malic enzyme B. In one preferred aspect of the present invention, said gene preferably has a DNA sequence of SEQ ID NO: 3.

In another aspect, the present invention relates to a recombinant vector containing the maeB gene and a recombinant microorganism obtained by introducing the maeB gene or the recombinant vector into a host cell selected from the group consisting of bacteria, yeast and mold.

In a still further aspect of the present invention, the recombinant vector is preferably pMVDmaeB, pMV19maeB, or pMEmaeB, but is not limited thereto. Additionally, the host cell is a succinic acid-producing microorganism, a lactic acid-producing microorganism, or an ethanol-producing microorganism. The succinic acid-producing microorganism is the genus *Mannheimia* microorganism, and preferably, the genus *Mannheimia* microorganism in which one or more pathways selected from the group consisting of an acetate-producing pathway, a lactate-producing pathway, a formate-producing pathway, an ethanol-producing pathway and an oxaloacetate-producing pathway, were blocked. More preferably, the succinic acid-producing microorganism is a *Mannheimia* sp. LPK (KCTC 10558BP) or LPK7.

As shown in a succinate synthesis pathway described more fully hereinafter with reference to FIG. 1, the maeB gene can convert malate to pyruvate. Thus, when the maeB gene is suitably expressed, it is possible to minimize malic acid that is produced as a byproduct in the production of succinic acid.

Accordingly, the present invention relates in another aspect to a method for preparing succinic acid, the method including the steps of: culturing the recombinant microorganism; and recovering succinic acid from the culture broth of the recombinant microorganism. The steps of culturing the recombinant microorganism and recovering the succinic acid can be carried out by the culture method and the isolation and purification method of succinic acid, which are generally known in the prior fermentation industry.

Additionally, by an increase in the production of pyruvate by the overexpression of the maeB gene, it is possible to increase the production of acetic acid, lactic acid or ethanol and to minimize the production of byproducts (succinic acid, malic acid and formic acid) in the preparation of acetic acid, lactic acid or ethanol. Thus, the present invention provides a method for preparing acetic acid, lactic acid or ethanol, the method including the steps of: culturing a microorganism producing acetic acid, lactic acid or ethanol, which is transformed with the maeB gene; and recovering lactic acid or ethanol from the microbial culture broth.

Other aspects, features and embodiments of the present invention will be more fully apparent from the following detailed description and appended claims.

DETAILED DESCRIPTION OF THE PREFERRED EMBODIMENT

The present invention is based on the discovery of a bacterial system for high productivity, low byproduct succinic acid production that overcomes the deficiencies of the prior art.

Figure 1:
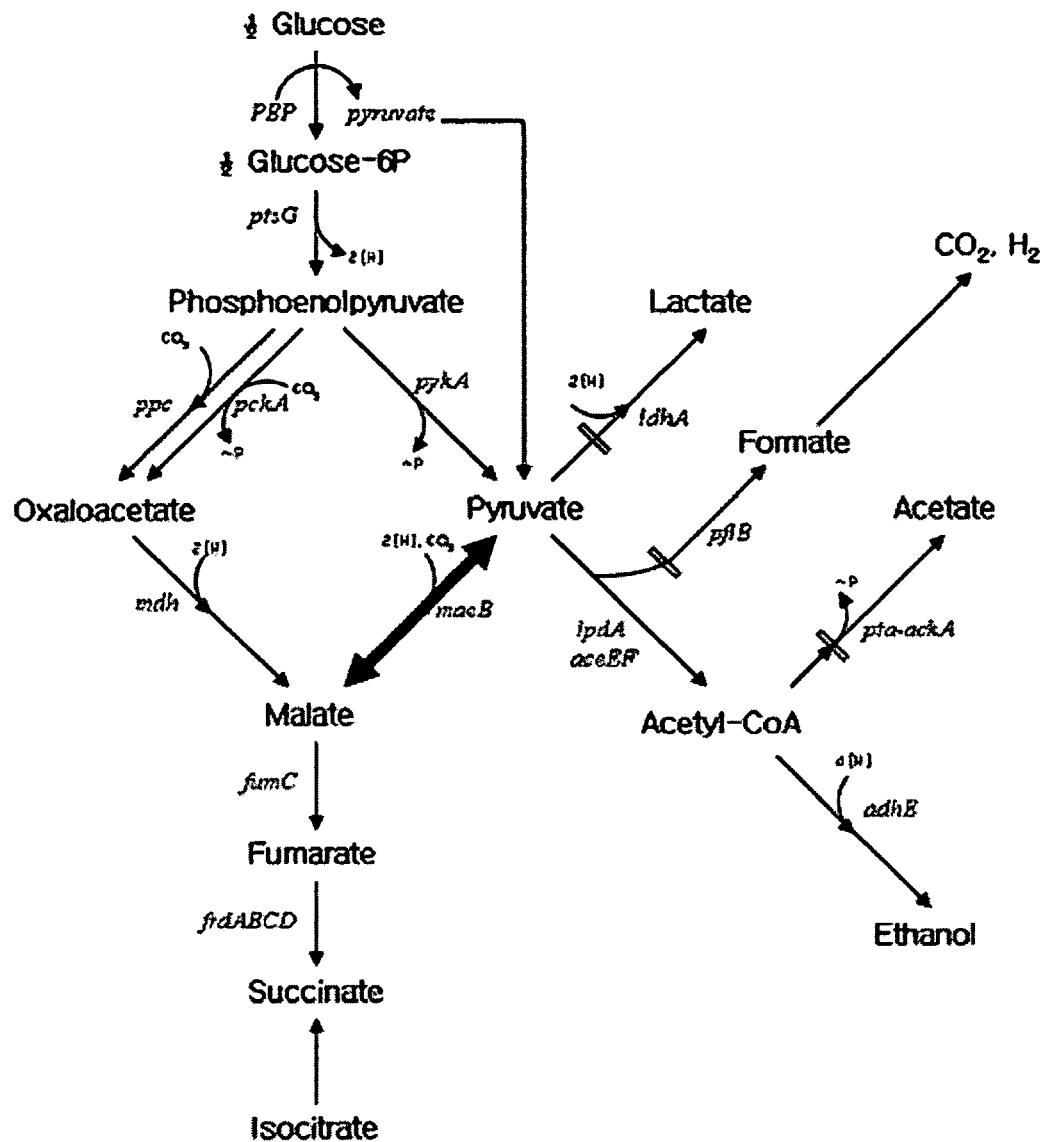
FIG. 1 is a schematic diagram showing a pathway for the synthesis of succinic acid from *Mannheimia* strain.

The present inventors have made extensive efforts to find the core gene involved in succinic acid metabolism in order to develop a microbial strain capable of minimizing the production of malate and of producing succinic acid with higher yield, on the basis of a succinic acid synthetic pathway shown in FIG. 1, and as a result, they have cloned a malic enzyme B-encoding gene (maeB) derived from *Mannheimia succiniciproducens* MBEL55E and determined the function thereof, thereby completing the present invention.

The present invention is more fully described hereinafter and with reference to illustrative examples. It is to be understood, however, that these examples are presented in order to more fully describe the present invention, and are correspondingly not intended to be construed to limit the present invention.

Although only the use of the specified expression vector and the genus *Mannheimia* microorganism which is a succinic acid-producing microorganism, as a host cell, to express the inventive gene, is illustrated in the following examples, the use of other kinds of expression vectors and succinic acid-producing microorganisms will be obvious to a person skilled in the art. Also, it will be readily apparent to a person skilled in the art that the known acetic acid-producing microorganism, lactic acid-producing microorganism and ethanol-producing microorganism in place of the succinic acid-producing microorganism can be used as a host cell.

EXAMPLE 1

Preparation of *Mannheimia/E. coli* Shuttle Vector pME

*Mannheimia/E. coli* shuttle vector pME was prepared from pMVSCS1 reported to be isolated from *Mannheimia* (Kehrenberg et al., *J. Antimicrob. Chemother.*, 49:383, 2002) and *E. coli* expression vector pKK223-3 (Amersham Pharmacia Biotech). For this purpose, pKK223-3 was partially digested with BamHI and AccI to collect a 2.7 kb fragment containing pBR322 ori and an ampicillin-resistant gene, and the single strand portions are filled with T4 DNA polymerase to make blunt ends. The blunt ends are ligated to prepare pKKD (2.7 kb). pMVSCS1 (5.6 kb) was digested with XhoII, and ligated with pKKD digested with restriction enzyme BamHI, to prepare fusion vector pMVD (8.3 kb). The pMVD was digested with NcoI, and a 5.9 kb fragment was religated to construct *Mannheimia/E. coli* shuttle vector pME.

EXAMPLE 2

Identification of Novel Gene (maeB) Derived from *Mannheimia Succiniciproducens* MBEL55E and Preparation of a Recombinant Plasmid Introduced with maeB Gene A malic enzyme-encoding gene of SEQ ID NO: 3 derived from *Mannheimia succiniciproducens* MBEL55E (KCTC 0769BP) was cloned, including a promoter and a transcription termination sequence.

Figure 2:
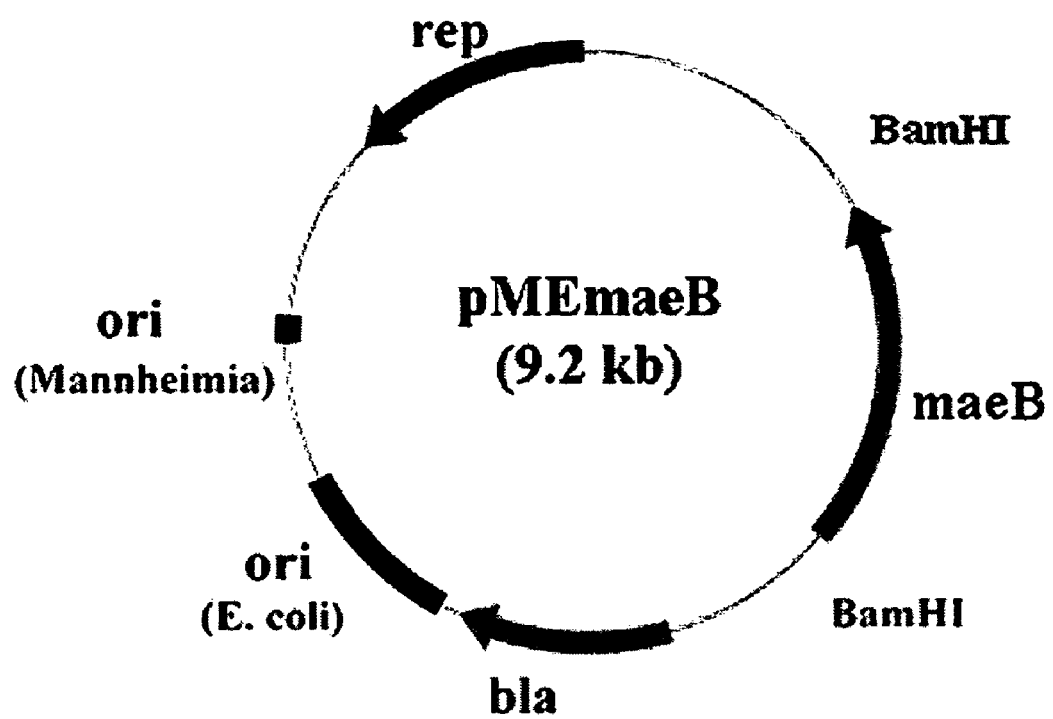
FIG. 2 is a gene map of recombinant plasmid pMEmaeB.

For this purpose, the chromosome of *Mannheimia succiniciproducens* MBEL55E as a template was subjected to PCR with primers of SEQ ID NOs: 1 and 2, under conditions shown in Table 1 below. The resulting maeB gene was digested with restriction enzyme BamHI and ligated to *Mannheimia/E. coli* shuttle vector pME digested with the same restriction enzyme to construct plasmid pMEmaeB (FIG. 2). In this way, a malic enzyme-encoding gene (maeB) derived from *Mannheimia succiniciproducens* MBEL55E was cloned.

TABLE 1

Conditions for amplification of maeB gene.

| Gene | Primer | Restriction enzyme site contained in the primer | Reaction condition |
|---|---|---|---|
| maeB | maeB-F(SEQ ID NO: 1), maeB-R(SEQ ID NO: 2) | BamH☐ | Cycle ☐: 94☐, 5 min<br>Cycle ☐: (30 cycles)<br>  94☐, 40 sec<br>  62☐, 30 sec<br>  72☐, 3 min<br>Cycle ☐: 72☐, 5 min<br>Cycle ☐: 4☐, forever |

The DNA sequence of the cloned maeB of *Mannheimia succiniciproducens* MBEL55E was analyzed and the amino acid sequence of malic enzyme B was presumed. As a result, the maeB gene of *Mannheimia succiniciproducens* MBEL55E had a DNA sequence of 2,271 bp (SEQ ID NO: 3), and the malic enzyme B consisted of 757 amino acid residues (SEQ ID NO: 4).

The homology of the maeB DNA sequence derived from *Mannheimia succiniciproducens* MBEL55E was analyzed, and as a result, this gene showed the highest homology of 82% (score: 196) with the malic enzyme of *Haemophilus ducreyi* 35000HP, a homology of 80% (score: 194) with the malic enzyme of *Haemophilus influenza* Rd KW20, and a homology of 81% (score: 145) with the malic enzyme of *Escherichia coli* CFT073. Although there were studies on an NAD-dependent *E. coli*-derived sfcA which is a malic enzyme gene, and the utilization thereof (Phue et al., *Biotechnol. Bioeng.*, 90:805, 2005), *Mannheimia succiniciproducens* MBEL55E has no sfcA gene and contains a NADP-dependent malic enzyme B-encoding gene maeB with the function similar to the sfcA gene.

It was reported that *Actinobacillus* sp. known to produce a large amount of succinic acid together with *Mannheimia* showed about 6-8 times reduction in NADP-dependent malic enzyme activity when it was fermented with the addition of fumarate which is a product of malic enzyme reaction (Van der Werf et al., *Arch. Microbiol.*, 167:332, 1997). However, there are still no genome sequence of malic enzyme B and example showing the cloning and expression of the malic enzyme B.

The G+C amount of the *Mannheimia succiniciproducens* MBEL55E maeB was found to be 46.2% which is higher than 38.5% for a *Haemophilus influenza* 86-028NP maeA gene but lower than 54.3% for an *Escherichia coli* CFT073 maeB gene. Meanwhile, the frequency of using amino acid codons in the *Mannheimia succiniciproducens* MBEL55E maeB gene was examined and the results are shown in Table 2 below. As shown in Table 2 below, the frequency of using amino acid codons in the maeB gene showed a different result from that in generally known *E. coli*. For example, for the frequency of using lysine codons, AAA was used at a high frequency of 98% in the *Mannheimia succiniciproducens* MBEL55E maeB gene, but AAA and AAG were used at frequencies of 76% and 24%, respectively in generally known *E. coil*. For the frequency of using glutamate codons, GAA was used at a frequency of 94% in the *Mannheimia succiniciproducens* MBEL55E maeB gene, but GAA and GAG in *E. coli* were used at frequencies of 70% and 30%, respectively. Also, for the frequency of using glutamine codons, CAA and CAG were used at frequencies of 79% and 21%, respectively in the *Mannheimia succiniciproducens* MBEL55E maeB gene, but at frequencies of 31% and 69%, respectively in *E. coli*.

TABLE 2

Frequency of using amino acid codons

| Amino acid | Codon | Frequency of use in MBEL55E maeB | Average frequency of use in *E. coli* |
|---|---|---|---|
| Ala | GCA | 0.20 | 0.22 |
|  | GCC | 0.24 | 0.25 |
|  | GCG | 0.43 | 0.34 |
|  | GCT | 0.14 | 0.19 |
| Arg | AGA | — | 0.04 |
|  | AGG | — | 0.03 |
|  | CGA | — | 0.05 |
|  | CGC | 0.55 | 0.37 |
|  | CGG | — | 0.08 |
|  | CGT | 0.45 | 0.42 |
| Asn | AAC | 0.30 | 0.61 |
|  | AAT | 0.70 | 0.39 |
|  | GAC | — | 0.41 |
|  | GAT | — | 0.59 |
| Cys | TGC | 0.56 | 0.57 |
|  | TGT | 0.44 | 0.43 |
| STOP | TAA | — | 0.62 |
|  | TAG | — | 0.09 |
|  | TGA | — | 0.30 |
| Gln | CAA | 0.79 | 0.31 |
|  | CAG | 0.21 | 0.69 |
| Glu | GAA | 0.94 | 0.70 |
|  | GAG | 0.06 | 0.30 |
| Gly | GGA | 0.14 | 0.09 |
|  | GGC | 0.35 | 0.40 |
|  | GGG | 0.06 | 0.13 |
|  | GGT | 0.45 | 0.38 |
| His | CAC | 0.56 | 0.48 |
|  | CAT | 0.44 | 0.52 |
| Ile | ATA | 0.02 | 0.07 |
|  | ATC | 0.38 | 0.46 |
|  | ATT | 0.61 | 0.47 |
| Leu | CTA | 0.04 | 0.03 |
|  | CTC | 0.12 | 0.10 |
|  | CTG | 0.12 | 0.55 |
|  | CTT | 0.11 | 0.10 |
|  | TTA | 0.45 | 0.11 |
|  | TTG | 0.17 | 0.11 |
| Lys | AAA | 0.98 | 0.76 |
|  | AAG | 0.02 | 0.24 |
| Met | ATG | 1.00 | 1.00 |
| Phe | TTC | 0.63 | 0.49 |
|  | TTT | 0.38 | 0.51 |
| Pro | CCA | 0.05 | 0.20 |
|  | CCC | 0.13 | 0.10 |
|  | CCG | 0.63 | 0.55 |
|  | CCT | 0.20 | 0.16 |
| Ser | AGC | 0.17 | 0.27 |
|  | AGT | 0.08 | 0.13 |
|  | TCA | 0.14 | 0.12 |
|  | TCC | 0.22 | 0.17 |
|  | TCG | 0.17 | 0.13 |
|  | TCT | 0.22 | 0.19 |
| Thr | ACA | — | 0.12 |
|  | ACC | — | 0.43 |
|  | ACG | — | 0.23 |
|  | ACT | — | 0.21 |
| Trp | TGG | 1.00 | 1.00 |
| Tyr | TAC | 0.40 | 0.47 |
|  | TAT | 0.60 | 0.53 |

TABLE 2-continued

Frequency of using amino acid codons

| Amino acid | Codon | Frequency of use in MBEL55E maeB | Average frequency of use in E. coli |
|---|---|---|---|
| Val | GTA | 0.22 | 0.17 |
| | GTC | 0.14 | 0.20 |
| | GTG | 0.29 | 0.34 |
| | GTT | 0.34 | 0.29 |

EXAMPLE 3

Production of Succinic Acid by Use of Transformed *Mannheimia*

The recombinant plasmid pMEmaeB constructed in Example 2 was transformed into *Mannheimia* LPK7 (KCTC 10626BP) by electroporation to prepare LPK7pMEmaeB. Also, pME was introduced into *Mannheimia* LPK7 (KCTC 10626BP) to prepare LPK7pME.

Each of the prepared recombinant strains was inoculated in 10 ml of a complex medium containing 9 g/l of glucose and cultured in an anaerobic condition at 39° C. for 16 hours. Each of the cultured strains was transferred in 250 ml of a complex medium containing 9 g/l of glucose and further cultured in the medium at 39° C. At this time, 100 µg/l of ampicillin as an antibiotic was added. The fermentation of each of the strains was performed by inoculating 250 ml of the *Mannheimia* culture broth in 2.5 L of a complex medium, and the fermentation conditions were as follows: initial glucose concentration: 20 g/l, pH: 6.8, and culture temperature: 39° C. For the adjustment of pH during the fermentation, ammonia solution (28%, v/v) was used, and the concentration of antibiotic ampicillin was the same as described above. A sample from each of the recombinant *Mannheimia* strains was collected during the fermentation, and the collected sample was centrifuged at 13,000 rpm and 4° C. for 10 minutes, and the concentrations of metabolites and succinic acid in the supernatant were analyzed by high-performance liquid chromatography (HPLC). The results are shown in Table 3 below.

As shown in Table 3, in the case where the recombinant plasmid pMEmaeB containing the maeB gene of MBEL55E was introduced into the recombinant *Mannheimia* LPK7 (accession number: KCTC 10626BP), the concentration of malate was reduced but the concentration of pyruvate was increased. These results suggest that the maeB gene of MBEL55E encodes an enzyme involved in the mutual conversion between malate and pyruvate during several steps of the succinic acid-producing pathway. The reduction rate of malate in LPK7 was 137% which is much higher than that in the control group.

Figure 3:
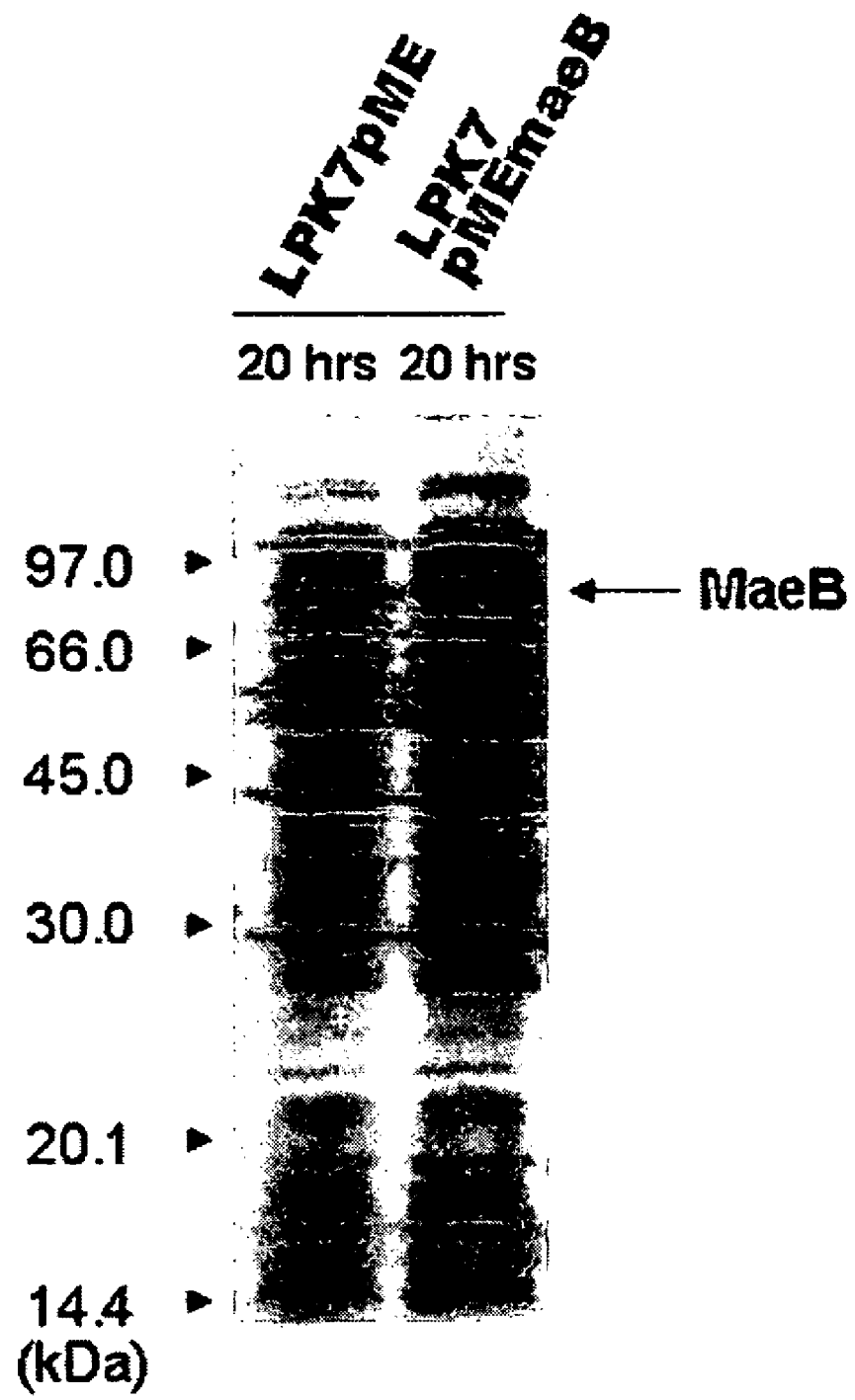
FIG. 3 is an SDS-PAGE showing the protein expression of recombinant *Mannheimia* LPK7pMEmaeB containing recombinant plasmid pMEmaeB.

Meanwhile, each of the strains was analyzed by SDS-PAGE, and the results are shown in FIG. 3. As can be seen in FIG. 3, the recombinant *Mannheimia* LPK7pMEmaeB transformed with the recombinant plasmid pMEmaeB showed a remarkable increase in the expression of malic enzyme B as compared to the recombinant *Mannheimia* LPKpME (control group) transformed with pME.

EXAMPLE 4

Measurement of Malic Enzyme Activity by Use of Transformed *Mannheimia*

The culture broth of *Mannheimia* LPK7pMEmaeB prepared in Example 3 was centrifuged at 13,000 rpm and 4° C. for 5 minutes. The precipitated cells were washed 2 times with an iced buffer solution (100 mM Tris-HCl (pH 7.0), 20 mM KCl, 5 mM MnSO$_4$, 2 mM DTT, 0.1 mM EDTA), and the washed cells were suspended in the same buffer and the cell membranes were disrupted by sonication. The cell debris were removed by a centrifugation, and the cell extract supernatant was used for the measurement of enzyme activity.

The enzyme activity of the cell extracts was measured with a spectrophotometer, in which the cell extract was allowed to react by adding a reaction buffer (0.1 M Tris-HCl (pH 7.8), 5 mM MgCl$_2$, 0.6 mM NADP+, 40 mM malate) to a 1 cm-width cuvette and adding the cell extract to the reaction buffer to a final volume of 1 ml, and the NADPH at 340 nm was measured. The results are shown in Table 4.

As shown in Table 4, the LPK7pMEmaeB cell extract showed 120% increase in enzyme activity compared to the LPK7pME cell extract. This result confirms that the maeB gene according to the present invention is a gene encoding malic enzyme B having the activity of either converting pyruvate to malate or converting malate to pyruvate.

TABLE 4

Enzyme activity of transformed *Mannheimia* strains

| Strain | Plasmid | *Enzyme activity (U) | Enzyme activity increase (%) |
|---|---|---|---|
| LPK7 | pME | 20.8 | 100 |
| LPK7 | pMEmaeB | 25.1 | 120 |

*Enzyme activity shows the titer of malic enzyme contained in 1 mg of total protein. An enzyme activity of 1.0 U is defined as the amount of enzyme required for converting 1 nmole of a substrate to a certain product at 37° C. for 1 minute.

The activity of the malic enzyme according to the present invention was compared to the known enzyme, and the result is shown in Table 5 below. As shown in Table 5, the malic enzyme of the *Mannheimia* strain transformed with the inventive maeB gene showed much higher activity than the malic enzyme of *E. coli* K12 (Gray et al., *Biochim. Biophys. Acta*, 117:33, 1966).

TABLE 3

Concentrations of malate and pyruvate in fermentation of transformed *Mannheimia*

| Strain Plasmid | Fermentation time (hrs.) | Cell concentration (OD$_{600}$) | Malate concentration (g/l) | Pyruvic acid concentration (g/l) | Malate reduction rate (%) | Succinic acid concentration (g/l) |
|---|---|---|---|---|---|---|
| LPK7 pME | 25 | 3.08 | 2.58 | 2.40 | 100 | 12.98 |
| LPK7 pMEmaeB | 28 | 2.98 | 1.62 | 2.73 | 137 | 12.95 |

TABLE 5

Comparison of malic enzyme activities between transformed *Mannheimia* and *E. coli*

| Strain | Enzyme activity (U) | Gene homology (%) |
|---|---|---|
| LPK7pMEmaeB | 25.1 | 67.6 |
| *E. coli* K12 | <1 | |

As described and proven in detail above, the present invention provides a novel gene encoding the malic enzyme B. The nucleotide sequence of the maeB gene may be a DNA sequence of SEQ ID NO: 3, or a sequence having appropriate homology thereto (e.g., that is at least 85%, and more preferably is at least 90, 91, 92, 93, 94, 95, 96, 97, 98, or 99% homologous to the nucleotide sequence of SEQ ID NO: 3). The novel gene according to the present invention is useful to prepare a recombinant microorganism capable of effectively reducing malate produced as a byproduct in the production of succinic acid. Also, the expression of the maeB gene can lead to an increase in the production of pyruvate during the preparation of acetic acid, lactic acid or ethanol. Thus, the maeB gene can increase the production of acetic acid, lactic acid or ethanol, and is also useful to prepare a microorganism for minimizing the production of byproducts (succinate, malate and formate). Accordingly, the maeB gene according to the present invention will be useful in increasing the production of various metabolites in the operation of central metabolic pathways by the combination with a suitable metabolic pathway.

While the present invention has been described in detail with reference to specific features, it will be apparent to those skilled in the art that this description is illustrative only of a preferred embodiment and is not intended in any way to limit the scope of the present invention, as defined by the appended claims and equivalents thereof.

What is claimed is:

1. An isolated maeB gene encoding a malic enzyme B having the amino acid sequence of SEQ ID NO: 4.

2. The isolated maeB gene according to claim 1, which has the DNA sequence of SEQ ID NO: 3.

3. A isolated malic enzyme B having the amino acid sequence of SEQ ID NO: 4, which has the activity of either converting pyruvate to malate or converting malate to pyruvate.

4. A recombinant vector containing the isolated maeB gene encoding a malic enzyme B having the amino acid SEQ ID NO: 4 and having the activity of either converting pyruvate to malate or converting malate to pyruvate.

5. The recombinant vector according to claim 4, which is pMEmaeB.

6. A recombinant microorganism obtained by introducing an isolated maeB gene encoding a malic enzyme B having the amino acid sequence of SEQ ID NO: 4 and having the activity of either converting pyruvate to malate or converting malate to pyruvate, or the recombinant vector according to claim 4 into a host cell selected from the group consisting of bacteria, yeast and mold.

7. The recombinant microorganism according to claim 6, wherein the host cell is a succinic acid-producing microorganism.

8. The recombinant microorganism according to claim 7, wherein the succinic acid-producing microorganism is the genus *Mannheimia*.

9. The recombinant microorganism according to claim 7, wherein the succinic acid-producing microorganism has one or more pathways, selected from the group consisting of an acetate-producing pathway, a lactate-producing pathway, a formate-producing pathway, an ethanol-producing pathway and an oxaloacetate-producing pathway, blocked.

10. The recombinant microorganism according to claim 8, which is any one selected from the group consisting of *Mannheimia* sp. LPK and LPK7.

11. The recombinant microorganism according to claim 6, wherein the host cell is an acetic acid-producing microorganism.

12. The recombinant microorganism according to claim 6, wherein the host cell is a lactic acid-producing microorganism.

13. The recombinant microorganism according to claim 6, wherein the host cell is an ethanol-producing microorganism.

14. A method for preparing succinic acid, the method comprising the steps of: culturing the recombinant microorganism according to claim 7; and recovering succinic acid from the culture broth of the recombinant microorganism.

* * * * *